(12) United States Patent
Meyer et al.

(10) Patent No.: US 10,314,511 B2
(45) Date of Patent: Jun. 11, 2019

(54) IMAGE-BASED IDENTIFICATION OF MUSCLE ABNORMALITIES

(75) Inventors: Craig Meyer, Charlottesville, VA (US); Silvia Blemker, Charlottesville, VA (US); Geoffrey Handsfield, Charlottesville, VA (US); Mark F. Abel, Earlysville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1131 days.

(21) Appl. No.: 14/237,986

(22) PCT Filed: Aug. 13, 2012

(86) PCT No.: PCT/US2012/050591
§ 371 (c)(1),
(2), (4) Date: Aug. 7, 2014

(87) PCT Pub. No.: WO2013/023214
PCT Pub. Date: Feb. 14, 2013

(65) Prior Publication Data
US 2014/0364723 A1     Dec. 11, 2014

Related U.S. Application Data

(60) Provisional application No. 61/522,500, filed on Aug. 11, 2011.

(51) Int. Cl.
*A61B 5/055*     (2006.01)
*A61B 5/107*     (2006.01)
(Continued)

(52) U.S. Cl.
CPC ............ *A61B 5/055* (2013.01); *A61B 5/1073* (2013.01); *A61B 5/4519* (2013.01);
(Continued)

(58) Field of Classification Search
CPC ...... A61B 5/055; A61B 5/1073; A61B 5/4519; A61B 5/7275; G06T 17/00;
(Continued)

(56) References Cited

U.S. PATENT DOCUMENTS 5,435,310 A * 7/1995 Sheehan ............... B82Y 15/00
382/128
5,650,723 A * 7/1997 Meyer ................. G01R 33/446
324/307

(Continued)

FOREIGN PATENT DOCUMENTS

WO     1999064983 A1     12/1999

OTHER PUBLICATIONS

Second Examination Report in related Australian Patent Application No. 2012294232, dated May 12, 2015.
(Continued)

*Primary Examiner* — Ruth S Smith
(74) *Attorney, Agent, or Firm* — Meunier Carlin & Curfman LLC

(57) ABSTRACT

A method is provided for identifying a muscle abnormality. The method may include acquiring image data associated with a plurality of muscles in an area of interest of a living subject and generating a data model for the plurality of muscles based on the image data. The method further includes calculating the volume and/or length of one of the plurality of muscles based on the data model, and determining if the volume and/or length for the muscle, as calculated, deviates from volume and/or length associated with a healthy muscle. If it is determined that the volume and/or length for the muscle deviates from the volume and/or length associated with a healthy muscle, a muscle abnormality can be identified based on the deviation.

36 Claims, 19 Drawing Sheets

(51) Int. Cl.
*A61B 5/00* (2006.01)
*G06T 7/00* (2017.01)
*G06T 17/00* (2006.01)

(52) U.S. Cl.
CPC .......... *A61B 5/7275* (2013.01); *G06T 7/0012* (2013.01); *G06T 17/00* (2013.01); *G06T 2200/04* (2013.01); *G06T 2207/10088* (2013.01); *G06T 2207/20036* (2013.01)

(58) Field of Classification Search
CPC ....... G06T 2200/04; G06T 2207/10088; G06T 2207/20036; G06T 7/0012
See application file for complete search history.

(56) References Cited

U.S. PATENT DOCUMENTS

| | | |
|---|---|---|
| 6,585,647 B1 | 7/2003 | Winder |
| 2007/0053560 A1 | 3/2007 | Miller et al. |
| 2008/0009707 A1* | 1/2008 | Theriault ............... A61B 5/055 600/410 |
| 2009/0128553 A1 | 5/2009 | Perry et al. |

OTHER PUBLICATIONS

Extended European Search Report for related EP Application No. 128222254 dated May 20, 2015.

Dunn, A.J. et al., "MR imaging findings of anterior interosseous nerve lesions," Skeletal Radiol, 2007, pp. 1155-1162, 36(12), Springer.

Gilles, B. et al., "Musculoskeletal MRI segmentation using multi-resolution simplex meshes with medial representations," Med. Image. Anal., 2010, pp. 291-302, 14(3), Elsevier B.V.

Hajghanbari, B. et al., "MRI-Based 3D Shape Analysis of Thigh Muscles: Patients with Chronic Obstructive Pulmonary Disease Versus Healthy Adults," Acad Radiol, 2011, pp. 155-166, 18(2).

International Preliminary Report on Patentability dated Feb. 20, 2014.

Office Action received in related Australian Patent Application No. 2012294232, dated Jul. 25, 2014.

* cited by examiner

IMAGE-BASED IDENTIFICATION OF MUSCLE ABNORMALITIES

This application is being filed as a PCT International Patent Application in the name of University of Virginia Patent Foundation, a U.S. national corporation, Applicant for all countries except the U.S., and Craig Meyer, Silvia Blemker, Geoffrey Handsfield, and Mark Abel, all U.S. residents, Applicants for the designation of the U.S. only.

CROSS-REFERENCE TO RELATED PATENT APPLICATIONS

This application is a United States National Stage Application of, and claims the benefit pursuant to 35 U.S.C. § 371 of, International Patent Application Serial No. PCT/US2012/050591, filed on Aug. 13, 2012, which claims priority to and the benefit of, pursuant to 35 U.S.C. § 119(e), U.S. provisional patent application Ser. No. 61/552,500, filed Aug. 11, 2011, entitled "An MRI-Based Muscle-Modeling Tool for Diagnosing Muscle Impairments," by Craig Meyer, Silvia Blemker, Geoffrey Handsfield, and Mark Abel, the contents of which is incorporated by reference herein in its entirety.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [4] represents the 4th reference cited in the reference list, namely, Tan H, Meyer C H. Estimation of k-space trajectories in spiral MRI. *Magn Reson Med.* 2009 June; 61(6): 1396-404.

BACKGROUND

Orthopedic surgeries are common and can carry a very high cost, both financially and in terms of patient recovery time. Orthopedic procedures often target ligaments, menisci, cartilage, tendon, and bone, but the biomechanical problems associated with the underlying impairments may involve muscle dysfunction, as well. Surgeries may be overprescribed or misguided because muscle impairments are not assessed rigorously and may be overlooked as a result. There are currently no effective methods for clinicians to objectively assess the degree of muscle abnormalities in a patient. Manual strength measurements are used to approximate functionality, but these measurements are subjective and may not provide adequate information regarding individual muscles. Currently, clinicians are unable to accurately diagnose muscle strength and imbalance issues. As a result, the ability of clinicians to form customized rehabilitative strategies to address such issues is limited, and the patient may be subjected to unnecessary surgical treatments that are costly and invasive. Further, there exists a need for accurately examining specific muscle abnormalities associated with enhanced athletic or other above-normal muscle performance in certain persons.

It is with respect to these and other considerations that the various embodiments described below are presented.

SUMMARY

Concepts and technologies are described herein for image-based identification of muscle abnormalities. Through an implementation of the embodiments disclosed herein, a method may include acquiring image data associated with a plurality of muscles in an area of interest of a living subject, and generating a data model for the plurality of muscles based on the image data. The method further includes calculating the volume and/or length of one of the plurality of muscles based on the data model, and determining if the volume and/or length for the muscle, as calculated, deviates from volume and/or length associated with a healthy muscle. If the volume and/or length for the muscle deviates from the volume and/or length associated with a healthy muscle, a muscle abnormality can be identified based on the deviation. Further, the deviation may be used to identify muscle abnormalities other than muscle impairments, for example muscle volume and/or length associated with enhanced muscle performance among certain individuals.

The subject matter described herein may also be implemented in a computing system, as an apparatus, or as an article of manufacture such as a computer-readable storage medium. The features, functions, and advantages discussed herein can be achieved independently in various embodiments of the concepts and technologies disclosed herein, or may be combined in yet other embodiments, further details of which can be seen with reference to the following description and drawings.

BRIEF DESCRIPTION OF THE DRAWINGS

FIG. 10A shows linear scalings for muscles crossing three joints in the lower limb and FIG. 10B illustrates a linear relationship between muscle volume and bone volume for subjects ranging in age and body size, in accordance with one embodiment presented herein.

DETAILED DESCRIPTION

Figure 1:
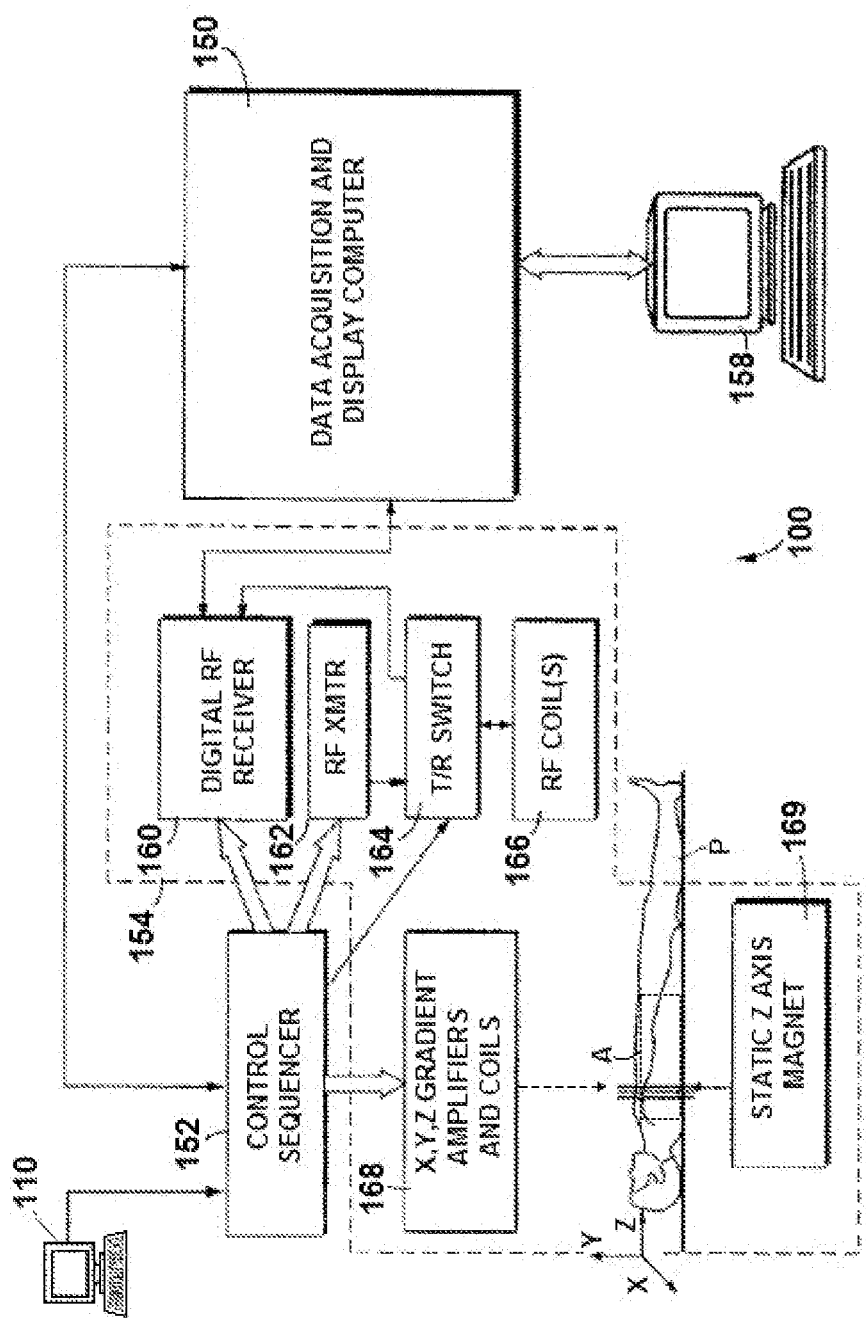
FIG. 1 is a system diagram illustrating an exemplary operating environment for various embodiments presented herein.

The following detailed description is directed to concepts and technologies for identification of muscle abnormalities. In the following detailed description, references are made to the accompanying drawings that form a part hereof and that show, by way of illustration, specific embodiments or examples. In referring to the drawings, like numerals represent like elements throughout the several figures.

FIG. 1 is a system diagram illustrating an exemplary operating environment for the various embodiments disclosed herein. Embodiments may be implemented on a commercial MRI system. FIG. 1 illustrates an example of such an MRI system 100, including a data acquisition and display computer 150 coupled to an operator console 110, a MRI real-time control sequencer 152, and a MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. Display 158 may be implemented through a variety of output interfaces, including a monitor, printer, or data storage. It should be appreciated that any number and type of computer-based tomography imaging systems or components, including various types of magnetic resonance imaging systems, may be used to practice aspects of the present disclosure, and the disclosure should not be limited to the exemplary type of MRI subsystem shown in FIG. 1.

Figure 2:
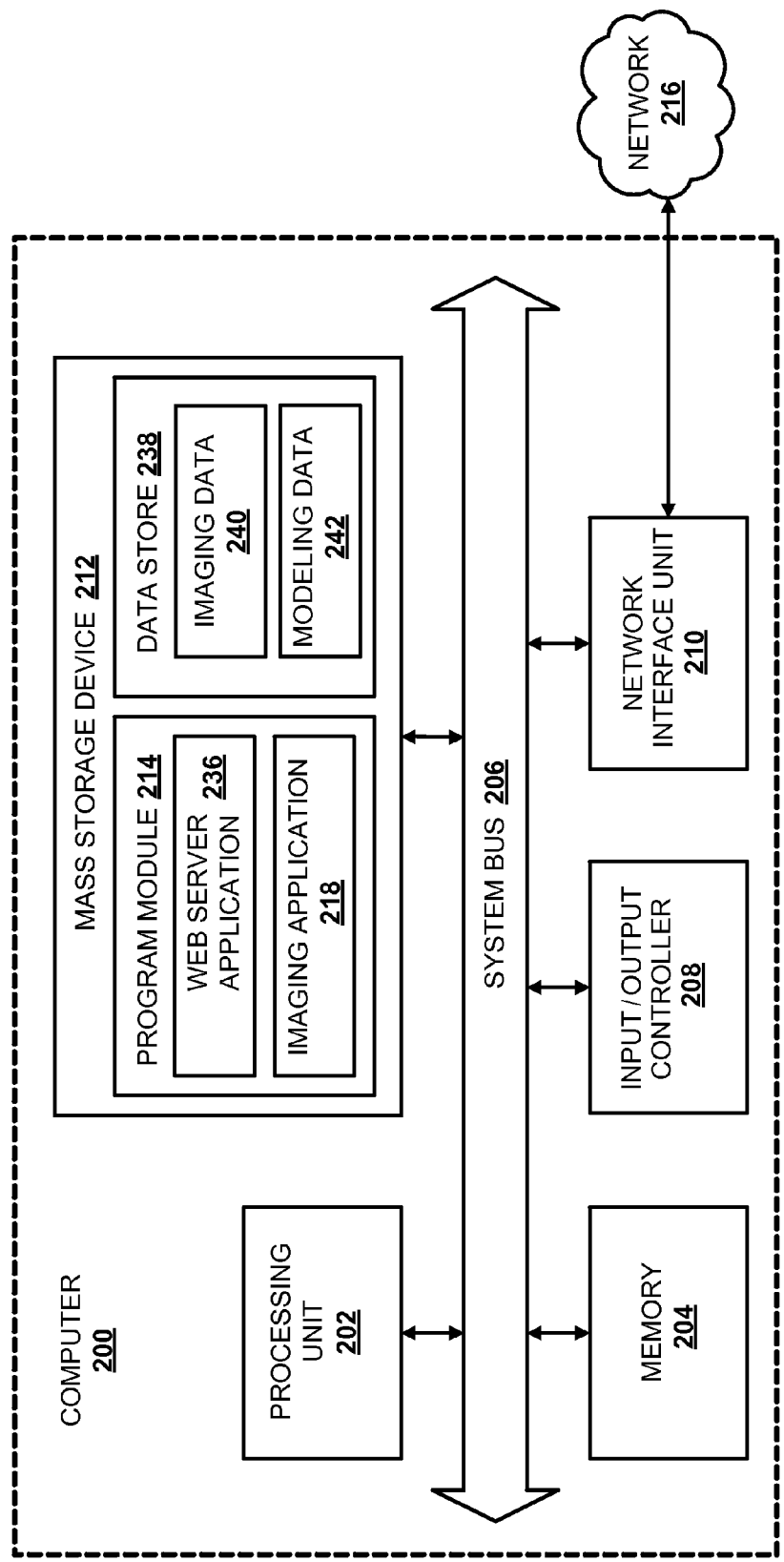
FIG. 2 is a computer architecture diagram showing illustrative computer hardware architecture for a computing system capable of implementing embodiments presented herein.

FIG. 2 is a computer architecture diagram showing illustrative computer hardware architecture for a computing system capable of implementing some embodiments presented herein. An example implementation of the computer 200 may include the data acquisition and display computer 150 of FIG. 1. The computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform various operations discussed below for identification of muscle abnormalities, and may include a web server application 236 and an imaging application 218. The computer can include a data store 238 for storing data that may include imaging-related data 240 such as image acquisition data, and a modeling data store 242 for storing imaging modeling data, or other various types of data utilized in practicing aspects of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example, and not limitation, computer-storage media may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200.

According to various embodiments, the computer 200 may operate in a networked environment using logical connections to remote computers through a network 216. The computer 200 may connect to the network 216 through a network interface unit 210 connected to the bus 206. It should be appreciated that the network interface unit 210 may also be utilized to connect to other types of networks and remote computer systems. The computer 200 may also include an input/output controller 208 for receiving and processing input from a number of input devices.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state, or may include rotating media storing magnetically-encoded information.

The program modules 214, which include the imaging application 218 may include software instructions that, when loaded into the processing unit 202 and executed, cause the computer 200 to provide functions for identification of muscle abnormalities, according to aspects of the disclosure described herein in accordance with exemplary embodiments. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202.

Encoding the program modules 214 may also transform the physical structure of the computer-storage media. The specific transformation of physical structure may depend on various factors, in different implementations of this description. Examples of such factors may include, but are not limited to: the technology used to implement the computer-storage media, whether the computer storage media are characterized as primary or secondary storage, and the like. For example, if the computer-storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer-storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Figure 3:
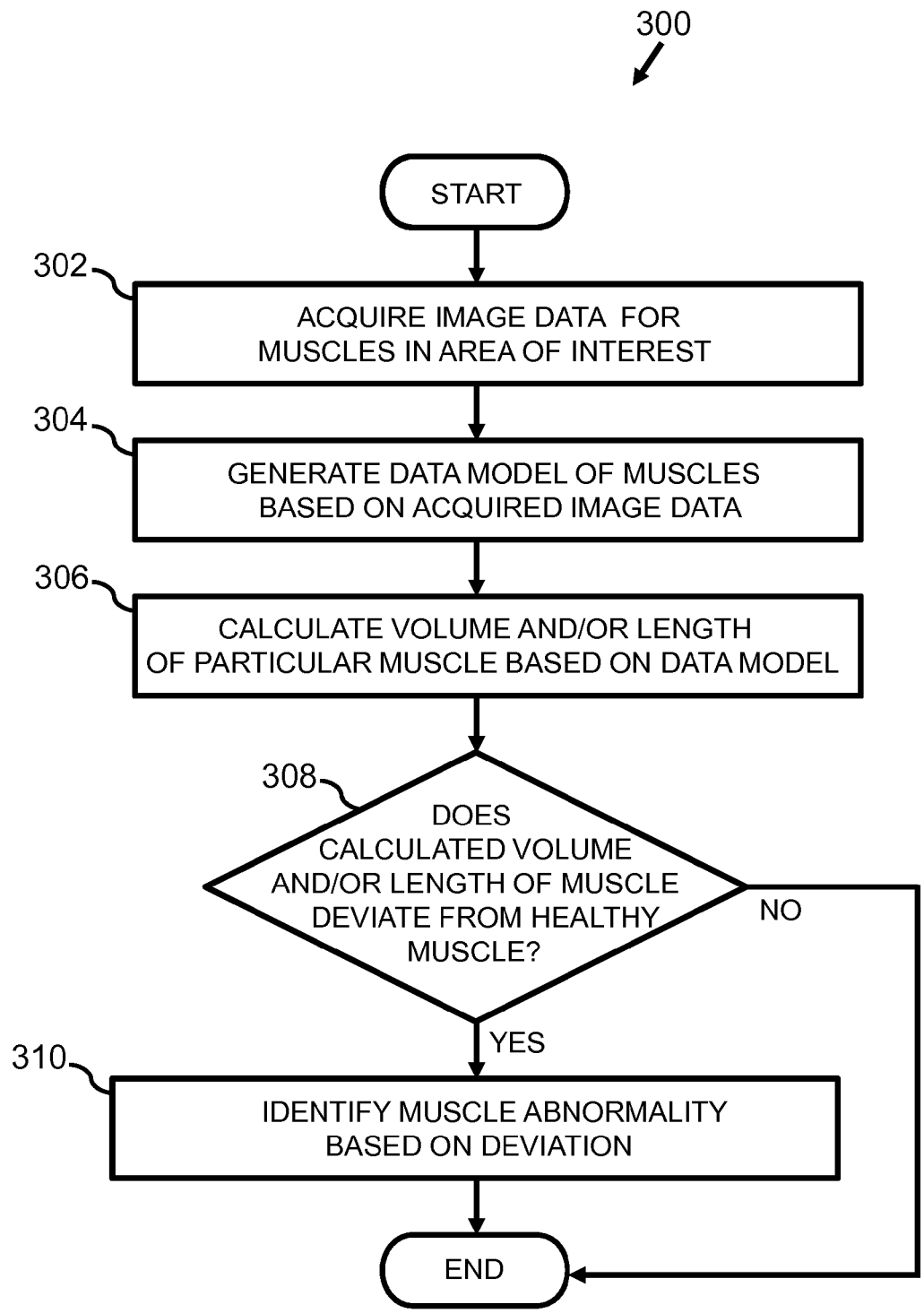
FIG. 3 is a flow diagram illustrating a method for identification of muscle abnormalities, in accordance with one embodiment presented herein.

Referring now to FIG. 3, an illustrative routine 300 will be described in detail, in accordance with one embodiment. In particular, FIG. 3 is a flow diagram illustrating a method for identifying a muscle abnormalities, in accordance with one embodiment. It should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states operations, structural devices, acts, or modules. These operations, structural devices, acts, and modules may be implemented in software, in firmware, in special purpose digital logic, and any combination thereof. It should be appreciated that more or fewer operations may be performed than shown in the figures and described herein. These operations may also be performed in a different order than those described herein.

The routine 300 begins at operation 302, where image data is acquired for muscles in an area of interest of a living subject. The routine 300 then proceeds to operation 304, where a data model corresponding to the muscles in the area of interest is generated based on the acquired image data. Next, at operation 306, the volume and/or length of a particular one of the muscles in the area of interest is calculated, based on the data model. From operation 306, the routine 300 proceeds to operation 308. At operation 308, a determination is made as to whether the calculated volume and/or length for the particular muscle deviates from the volume and/or length of a healthy muscle. As used herein, the term "healthy" when associated with a muscle may encompass a muscle that is associated with a normal individual from a population of persons with standard musculoskeletal structure, that is, individuals that do not have muscle impairments as discussed herein or are not associated with enhanced performance of one or more muscles, or resulting athletic functions, for instance, that would be abnormal as compared to the normal population. If the calculated volume and/or length deviates from the volume and/or length of the healthy muscle, then the routine 300 proceeds from operation 308 to operation 310. At operation 310, a muscle abnormality can be identified based on deviation, and the routine 300 then ends. If it is determined at operation 308 that the calculated volume and/or length of the particular muscle does not deviate from the volume and/or length of the healthy muscle, then the routine 300 ends.

Acquiring the image data may include receiving image data that is associated with spiral MRI scans of the area of interest of the living subject. Generating the data model comprises forming a three-dimensional model of the plurality of muscles based on the received image data associated with the at least one spiral MRI scan, of the muscles in the area of interest, based on the received image data associated with the spiral MRI scans. The imaging and/or reconstruction may include utilizing water-selective imaging or water/fat imaging. Spectral-spatial excitation pulses may be utilized to form water-selective images, but other methods can be used, alternatively. Also, spectral-spatial excitation pulses may be used for water/fat imaging. Interleaved multislice long-TR (or density-weighted) scans can be helpful for the delineation of different muscles. An image reconstruction for spiral scans that includes k-space trajectory estimation and off-resonance correction for both main field inhomogeneity and concomitant gradient fields.

The area of interest of the living subject may include a limb and/or a joint. For example, the area of interest may be comprised of muscles proximate to an elbow, knee, or shoulder joint, or may be comprised of muscles throughout a lower or upper limb such as a leg or arm, respectively. Calculating the volume and/or length of the particular muscle may include segmentation of the muscles in the area of interest based on muscle groups.

Identifying a muscle abnormality may include comparing the deviation to a predetermined threshold deviation, such that a deviation over the threshold would correspond to a muscle abnormality. For example, the threshold may be set such that a deviation exceeding the threshold represents muscle hypertrophy. Additionally or alternatively, the threshold may be set such that a deviation exceeding the threshold represents muscle atrophy. Visual representations can be generated that provide visual representations of the muscles and deviations, in the form of graphs, color-coded image reconstructions, plots, or other formats for visually representing data.

Additionally, or alternatively, identifying a muscle abnormality may include calculating a deviation factor that corresponds to the amount and/or degree of the deviation. A muscle abnormality may be identified by determining if the calculated deviation factor corresponds to a previously determined deviation factor that is associated with a muscle abnormality. A deviation factor may be calculated for a deviation in muscle volume and/or length ratio as compared to a healthy ratio. The healthy muscle, which as described above can be used for comparison against the particular muscle in the area of interest that has been imaged, may correspond to a muscle that is the same specific type of muscle as the muscle being imaged. The healthy muscle may represent a healthy muscle, or enhanced muscle, from only one healthy living subject, or the healthy muscle may represent a composite based on healthy muscle from several healthy living subjects in a sample population.

EXEMPLARY IMPLEMENTATIONS

The following describes examples of practicing concepts and technologies presented herein, and corresponding results, in accordance with aspects of the present disclosure. These examples are for illustrative purposes only. The disclosure herein is not limited to these examples.

Example 1

Figure 4A:
FIGS. 4A and 4B show preliminary muscle imaging and modeling, respectively, according to one embodiment presented herein.
Figure 4B:

Using information obtained from imaging and reconstruction of muscle morphology, one can measure volumes and lengths of all the major muscles of the entire lower extremity. FIGS. 4A and 4B show results of preliminary imaging and modeling, respectively. This technique requires a very simple and fast MRI scan which takes roughly 15 minutes and requires no specialized coils (only the body coil of the scanner is used). Spiral k-space scanning can be used to produce a very rapid protocol for proton density weighted imaging. Spiral scans intrinsically have very short echo times (TE)s, which provides an advantage for this implementation. The technique according to this Example collects a water-selective multi-slice spiral data set with a long repetition time (TR) (800-1000 ms) and reconstructs the images using gridding image reconstruction with semi-automatic off-resonance correction, as described in Holzbaur et al. [1] and in U.S. patent application Ser. No. 12/114,307. The technique corrects for both main field off-resonance effects and concomitant gradient effects, using a fast conjugate phase reconstruction algorithm based on a Chebyshev approximation, as described in Hurley [2] and in U.S. patent application Ser. No. 12/114,307. The water-selective excitation is performed using a spectral-spatial excitation, as described in Moseley et al. [3] and in U.S. Pat. No. 4,999,580. The k-space trajectory used in the image reconstruction is estimated using the model described in Tan et al. [4] and in U.S. Pat. No. 7,888,935.

The technique according to this Example collects a water-selective or water/fat multi-slice spiral data set with a long TR (800-1000 ms) and reconstructs the images using gridding image reconstruction with semi-automatic off-resonance correction, as described in Chen and Meyer [9] and in U.S. Pat. No. 8,238,634. The technique corrects for both main field off-resonance effects and concomitant gradient effects, using a fast conjugate phase reconstruction algorithm based on a Chebyshev approximation, as described in Chen et al. [5] and in U.S. Pat. No. 8,094,907. The water-selective or water/fat excitation is performed using a spectral-spatial excitation, as described in Meyer et al. [10] and in U.S. Pat. No. 4,999,580. The k-space trajectory used in the image reconstruction is estimated using the model described in Tan and Meyer [4] and in U.S. Pat. No. 7,888,935.

Figure 5:
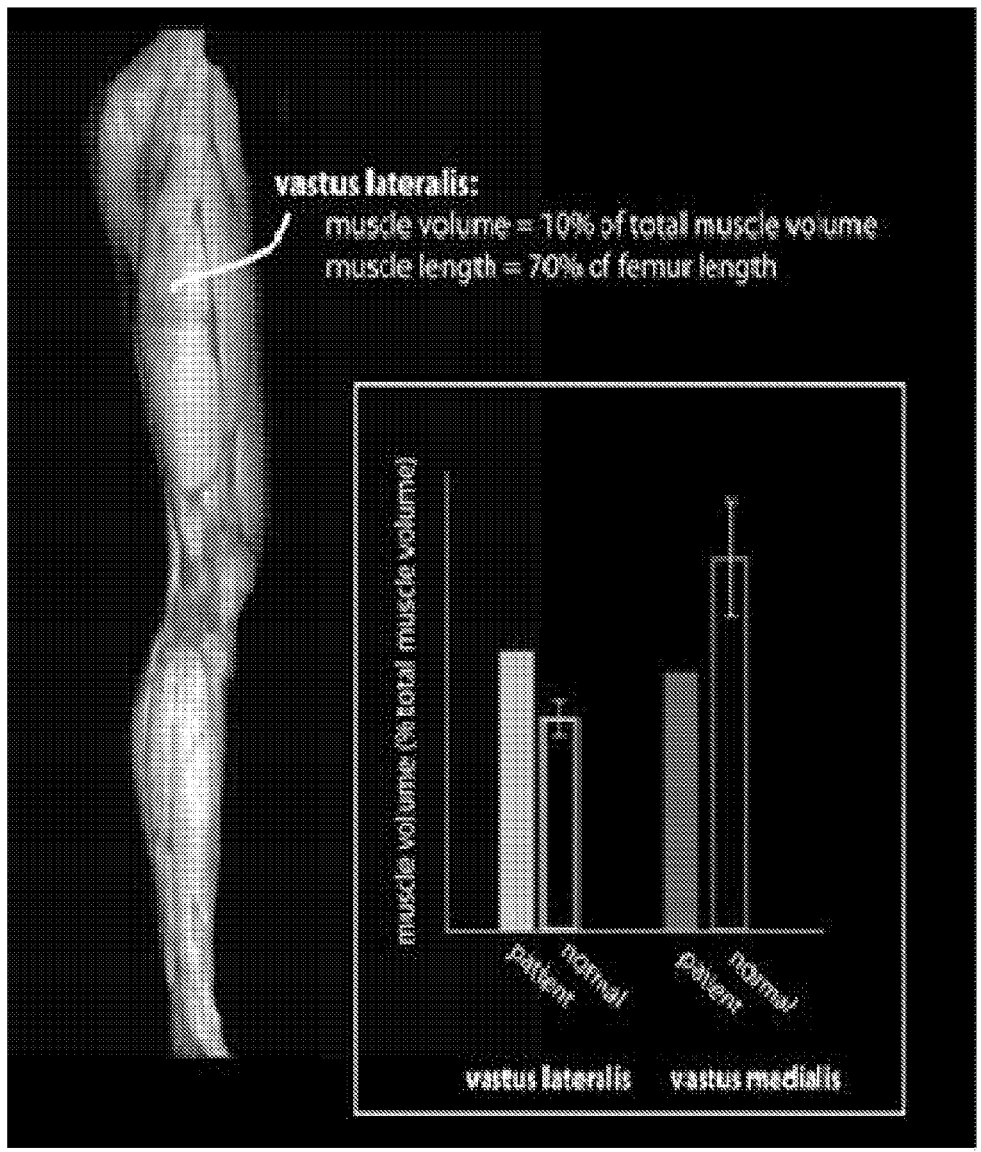
FIG. 5 illustrates a display from imaging analysis software, in accordance with one embodiment presented herein.

For image processing and modeling, based on a few sets of manual inputs, software in accordance with aspects of the present disclosure generates a three-dimensional reconstruction of each muscle in the lower extremity, along with a report of the relative volumes and lengths of all the muscles as compared to a group of adult healthy subjects. A user can select muscles of interest and the software will report volumes and lengths of these muscles of interest. Similarly, a report can be generated that identifies which muscles have volume and/or length ratios that are different from the average by at least one standard deviation. These features will allow clinicians to quickly isolate the impaired muscles. FIG. 5 illustrates a display of analysis software functionality. The software allows the user to highlight and isolate muscles of interest and the software generates graphs that allow the user to compare particular muscle lengths and volumes with adult healthy populations.

Example 2

Clinical assessments of gait impairments in patients with cerebral palsy (CP) involve global assessments of movement and function, which include a physical exam, visual observation of the patient's gait, motion capture data, and electromyographic measurements. These types of tests may be unable to determine strengths or weaknesses for individual muscles, but treatments for abnormal gait target individual muscle impairments. Identifying hypertrophy or atrophy of each muscle within a joint is needed to design more tailored treatments intended to improve the gait of CP subjects. In this Example, a fast, non-invasive imaging technique is reported, for assessing the specific muscle volumes in the lower limb of both healthy and CP subjects in vivo. In particular, this Example describes a non-invasive in vivo method for assessing the relative volumes of subjects with impaired gait. The technique demonstrates reliability in its prediction of a consistent mean muscle volume ratio among healthy subjects and precision in its detecting relative hypertrophy and atrophy at the individual muscle level among CP subjects.

Seven normal, healthy subjects (three female and four male, age: 24.6±3.5 years, height: 177.3±7.7 cm, weight: 71.9±11.1 kg) and four subjects with CP (one female and three male, age: 12.8±1.7 years, height: 151.2±11.9 cm, weight: 56.2±13.3 kg) were scanned feet first in the supine position in a 3T Siemens Trio MRI Scanner. A fast 2D multislice spiral gradient-echo protocol was used with the following imaging parameters: TE/TR/α: 3.8 ms/800 ms/90°, field of view: 400 mm×400 mm, slice thickness: 5 mm, spatial resolution: 1.1 mm×1.1 mm. A Chebyshev approximation was used for semi-automatic off-resonance correction [5]. Total imaging time was approximately ten minutes. Axial images were obtained from the iliac crest to the ankle joint.

The muscle bellies of the 34 muscles and muscle groups comprising the lower limb were segmented in axial slices using custom semi-automatic software. Volumes for each structure were determined voxel-wise by rendering structures in 3-D (FIG. 6). The muscle volume for the entire lower limb was determined by summing over all of the segmented muscle bellies. Muscle volume ratios were calculated for each muscle for the healthy population and for each CP subject: $R_{mv}=V_i/V_{tm}$. Muscles were categorized into groups according to the joint that they cross and the action that they perform on that joint (FIG. 7). For each subject, colormaps were made which display the number of standard deviations that the individual's muscle volume ratio deviates from the mean healthy muscle volume ratio (FIG. 8).

Results shows that there was a high degree of correlation between lower limb muscles grouped by joint and action among both healthy and CP subject groups. Regression lines shown are least squares linear fits to the healthy subjects only, giving a normal line of lower limb ratios. The $R^2$ values reported are for the entire population, illustrating that, with very good correlation, the CP subjects generally have the same volume ratios at each joint as the normal population. However, colormaps of the CP patients (FIG. 8) illustrate that there is significant atrophy and hypertrophy for specific muscles in a given CP subject compared to the normal population. Thus, despite consistency at the level of joint-crossing muscle groups for CP subjects, there is significant relative weakening and strengthening of individual muscles within those groups that is not detected by assessing joint-crossing groups alone. It is to be expected that abnormal gait patterns will result in changes in musculoskeletal structure as a subject's musculature will optimize for efficiency under an altered walk.

Figure 6D:
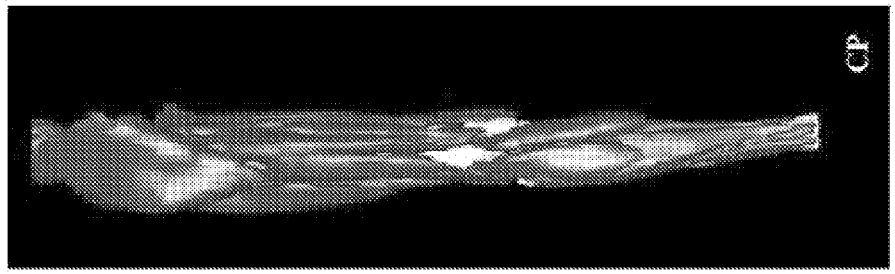
FIGS. 6C and 6D show 3-D reconstructions and volumes calculated for healthy and CP subjects, respectively, in accordance with one embodiment presented herein.
Figure 6C:
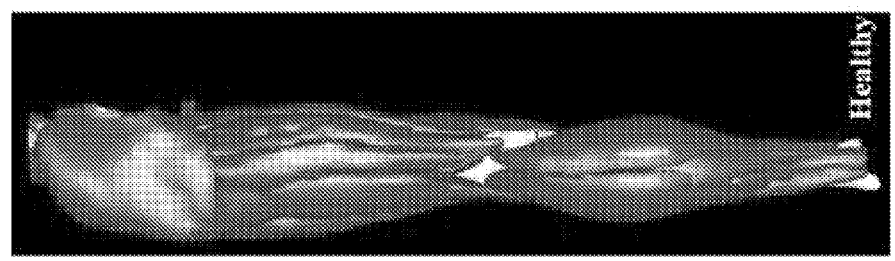
Figure 6A:
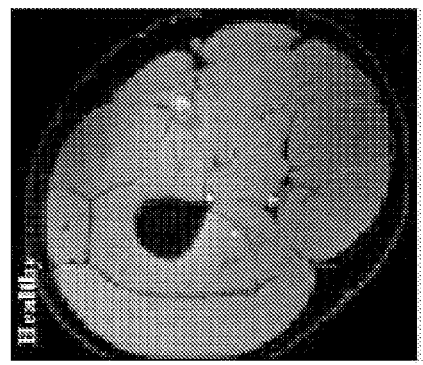
FIGS. 6A and 6B show axial images acquired and segmented for healthy subjects and subjects with cerebral palsy (CP), respectively.
Figure 6B:
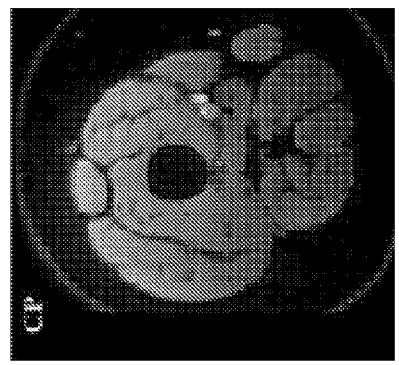
Figure 7A:
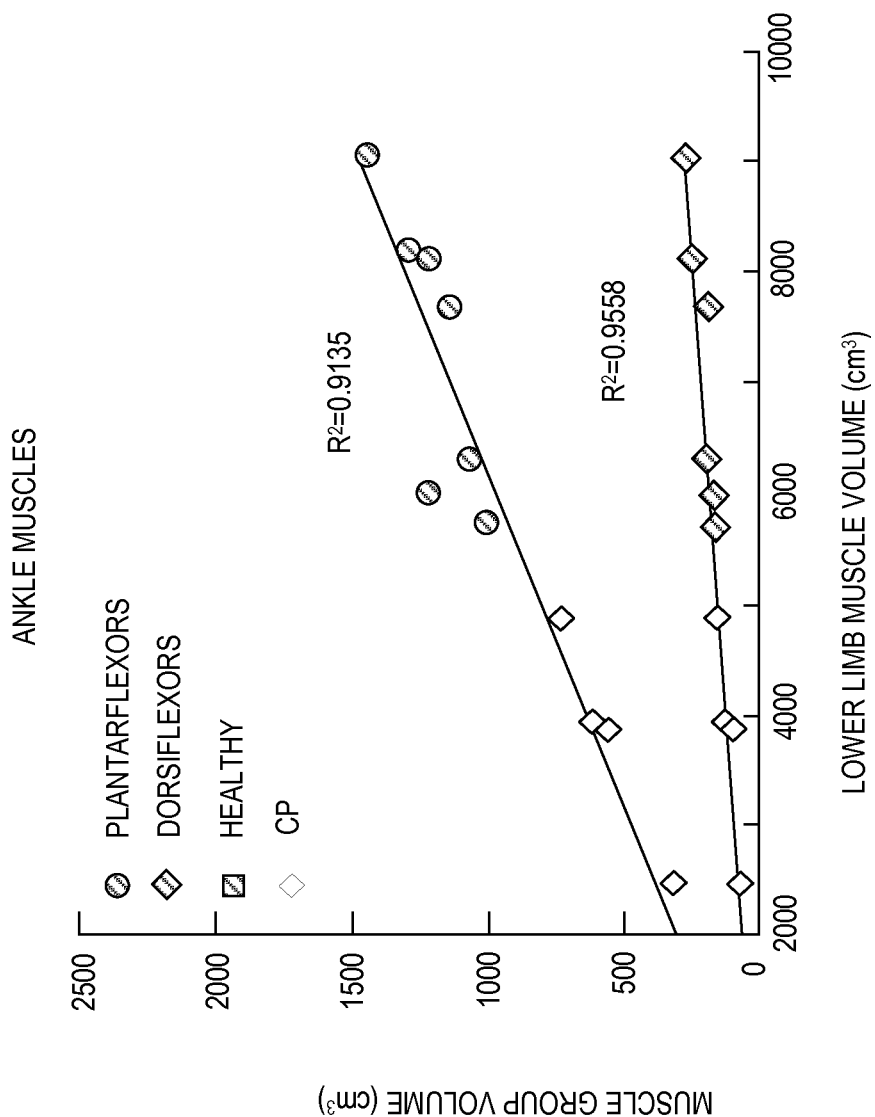
FIGS. 7A-7C show volume ratio plots for seven healthy and four CP subjects for muscles that cross the ankle (FIG. 7A), hip (FIG. 7B), and knee (FIG. 7C), in accordance with one embodiment presented herein.
Figure 7B:
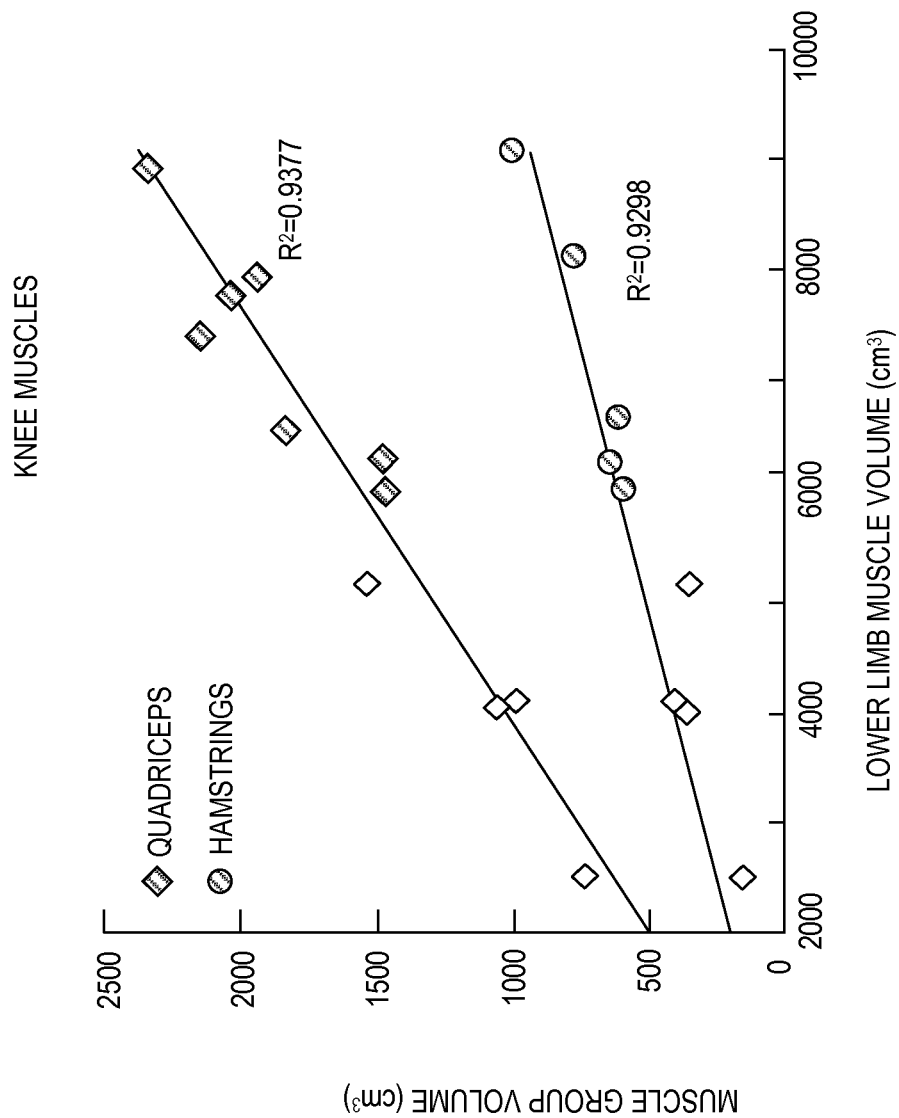
Figure 7C:
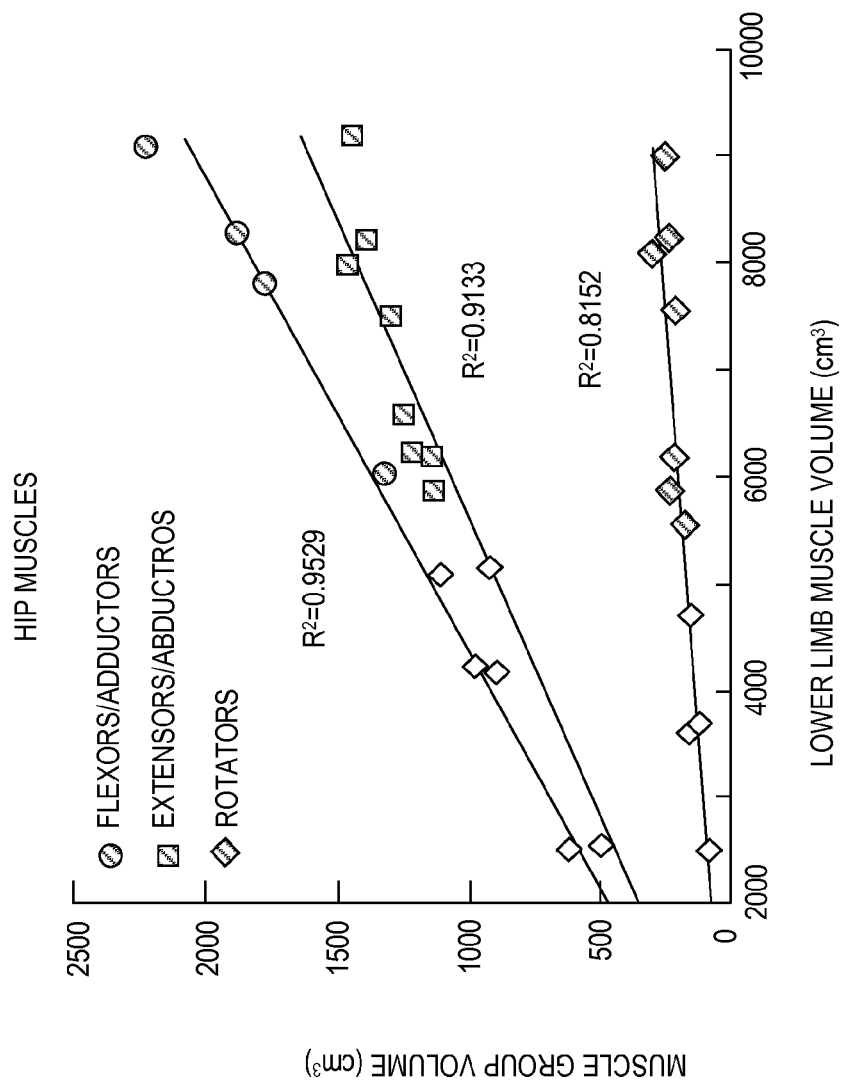
Figure 8A:
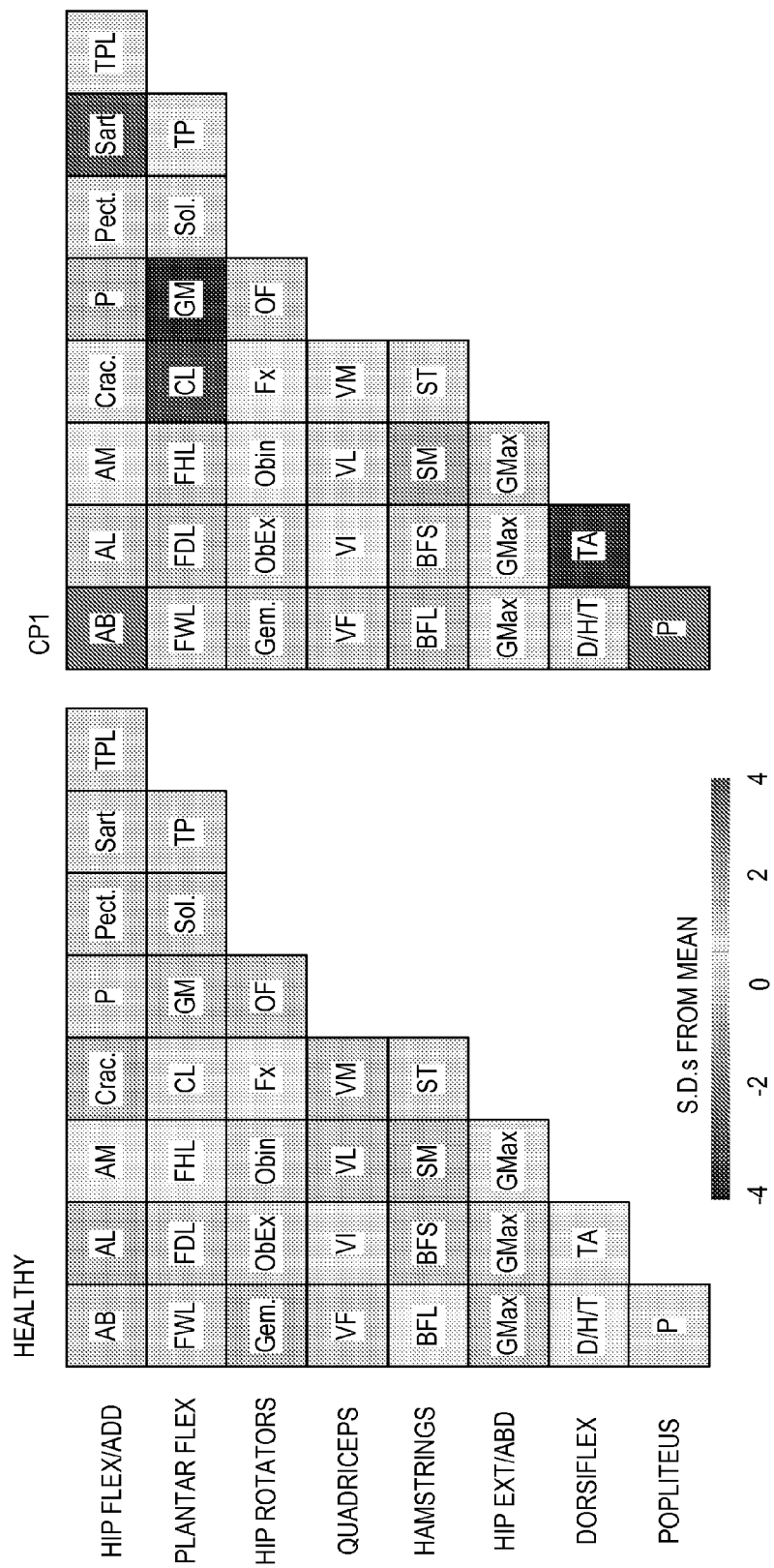
FIG. 8 illustrates colormaps generated for one healthy and four CP subjects, where rows represent joint/action groups while columns represent individual muscles, in accordance with one embodiment presented herein.
Figure 8B:
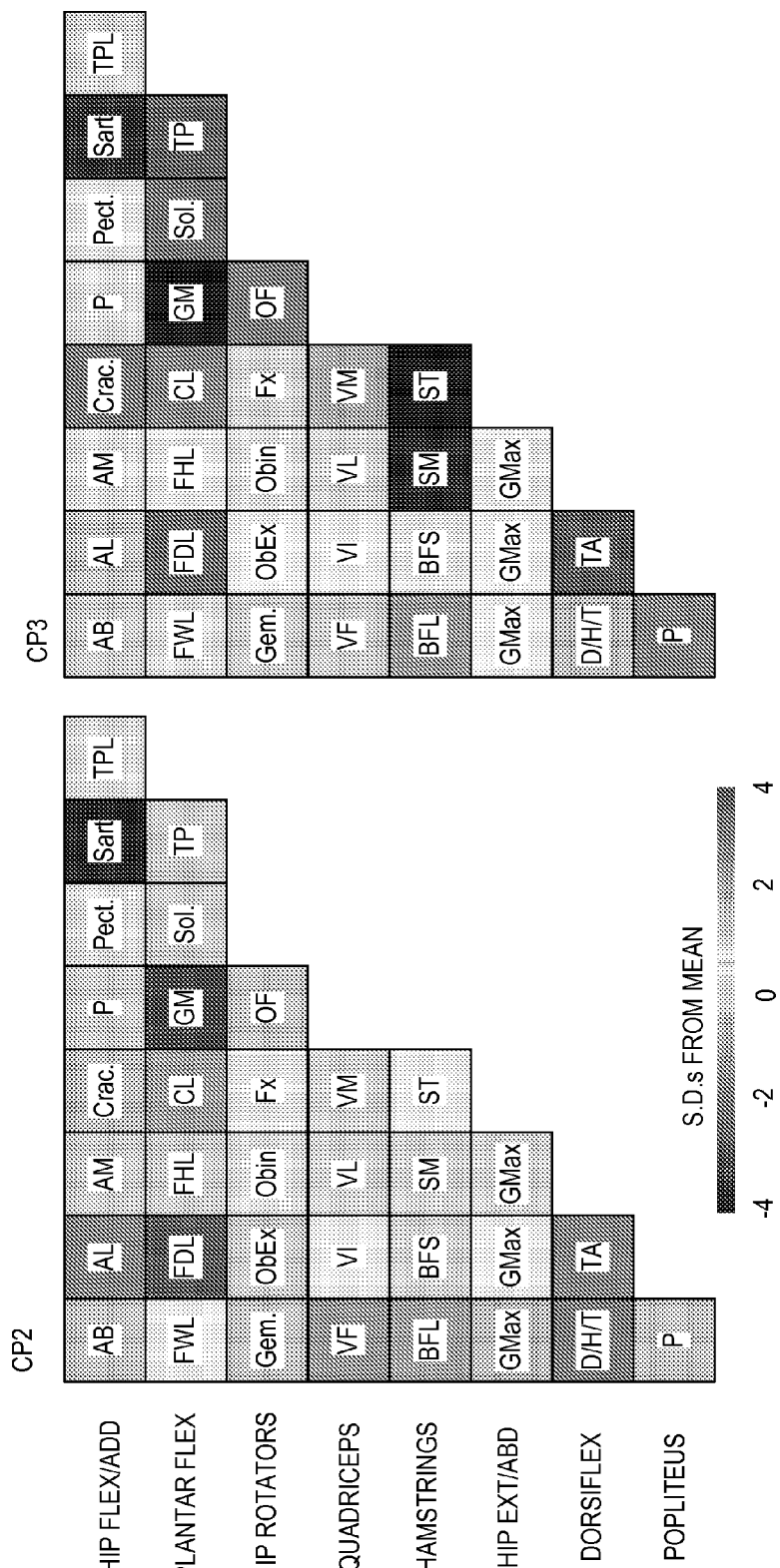
Figure 8C:
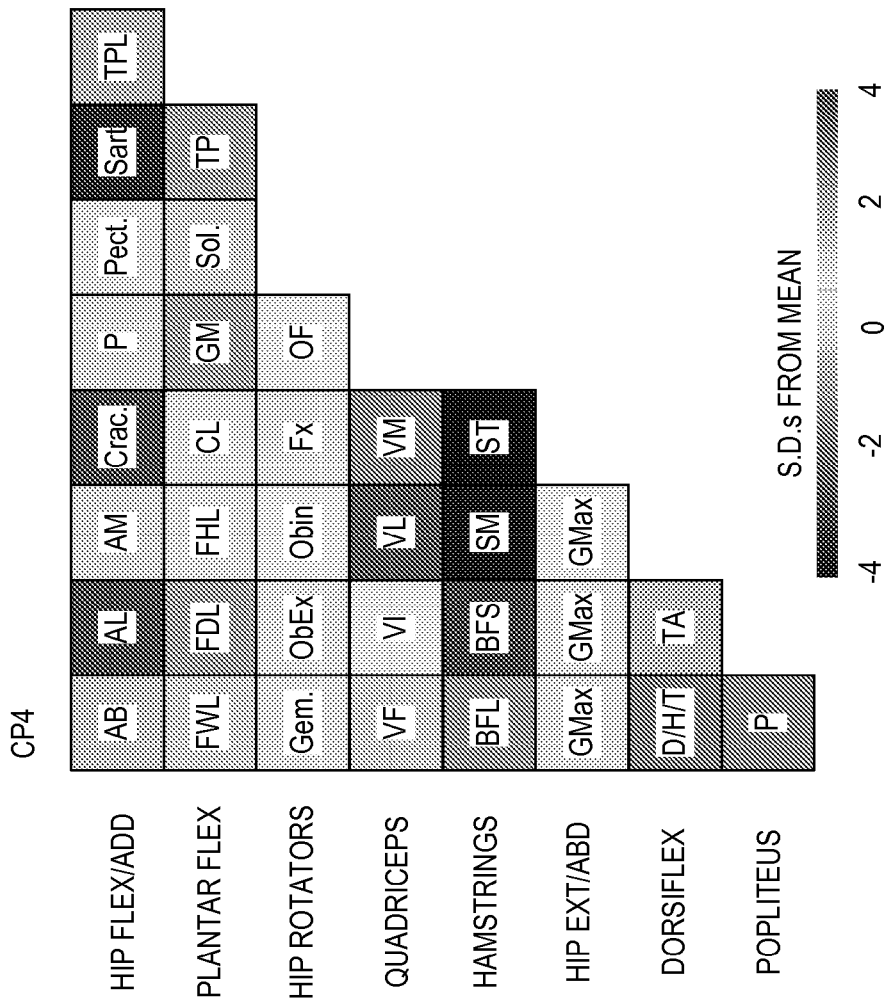

Now with particular reference to the illustrations in FIGS. 6-8, FIG. 6 provides an illustration of aspects of the technique used in this Example, where FIGS. 6A and 6B show axial images acquired and segmented for healthy (FIG. 6A) and CP (FIG. 6B) subjects. 3-D reconstructions (posterior view shown) were generated and volumes calculated for healthy (FIG. 6C) and CP (FIG. 6D) subjects. FIG. 7 shows volume ratio plots for seven healthy (filled symbols) and four CP (open symbols) subjects for muscles that cross the ankle (FIG. 7A), hip (FIG. 7B), and knee (FIG. 7C). Trendlines were generated using linear regression for the seven healthy subjects only. $R^2$ values are for the entire population of eleven subjects with respect to the healthy trendline. FIG. 8 illustrates colormaps generated for one healthy and four CP subjects. Rows represent joint/action groups while columns represent individual muscles. The colorbar is in units of healthy standard deviations (S.D.) and the scale is −4 S.D. to +4 S.D. The muscles represented in the colorbars are as follows: AB: adductors brevis, AL: adductor longus, AM: adductor magnus, Grac: gracilis, IP: iliopsoas, Pect: pectineus, Sart: sartorius, TFL: tensor fascia latae, FB/L: fibularis brevis/longus, FDL: flexor digitorum longus, FHL: flexor hallucis longus, GL: lateral gastroc, GM: medial gastroc, Sol: soleus, TP: tibialis posterior, Gem: sup/inf gemellus, ObEx: obturator externus, ObIn: obturator internus, Pir: piriformis, QF: quadratus femoris, RF: rectus femoris, VI: vastus intermedius, VL: vastus lateralis, VM: vastus medialis, BFL: biceps femoris longhead, BFS: biceps femoris shorthead, SM: semimembranosus, ST: semitendinosus, GMax: gluteus max, GMed: gluteus medius, GMin: gluteus minimus, D/H/T: extensor digitorum longus/extensor hallucis longus/fibularis tertius, TA: tibialis anterior, and P: popliteus.

The results from the implementations according to this example show, among other advantages, a non-invasive in vivo method for assessing the relative volumes of subjects with impaired gait. The data and above description of the technique demonstrates reliability in its prediction of a consistent mean muscle volume ratio among healthy subjects and precision in its detecting relative hypertrophy and atrophy at the individual muscle level among CP subjects.

Example 3

Determination of scaling relationships for musculoskeletal architecture is important for understanding fundamental shape and size principles in biology, estimating clinical subject parameters, and generating realistic musculoskeletal models. Currently, only limited knowledge exists on how muscle sizes may scale across individuals. Moreover, most currently used architecture data are based on cadaveric studies, which typically represent elderly populations and may not represent the muscle architecture for active, healthy individuals. In the study described herein for this Example, magnetic resonance (MR) images were collected of the lower limb of a cohort of young healthy adults and adolescent boys in order to show how muscle volumes scale with height and mass, how individual muscle volumes scale relative to each other, and how muscle volumes scale with bone volume.

Ten healthy adults (five women) with the following parameters (mean±S.D.): age: 25.2±4 years, height: 175±9 cm, weight: 69.8±12.1 kg and five healthy adolescent boys: 13.8±0.8 years, 167.8±6.5 cm, 65.0±11.2 kg, all with no prior history of lower limb injury, were scanned on a 3T Siemens Trio MRI scanner. Axial images were acquired from the twelfth thoracic vertebra to the ankle joint using a non-Cartesian gradient echo sequence. Scanning parameters were as follows: TE/TR/α: 3.8 ms/800 ms/90°, field of view: 400 mm×400 mm, slice thickness: 5 mm, in plane spatial resolution: 1.1 mm×1.1 mm. Additionally, a Chebyshev approximation was applied for semi-automatic off-resonance correction [5]. Thirty-five muscles in the hip, knee, and ankle were segmented using a segmentation program written in Matlab. The volumes of each muscle and bone in the lower limb were calculated. The volumes of all of the muscles and all of the bones were summed for each subject to obtain the total muscle volume and total bone volume, respectively, of the limb.

These data allowed the relationship between total muscle volume of the lower limb and subject parameters, such as mass and height, to be probed. In this Example, an analytical mechanical model of the lower limb (FIG. 9A) was used to predict this relationship. Briefly, muscle volume has been previously related to muscle torque [6]:

$$T_{muscle} \alpha V_{muscle}$$

The torque needed to support a human standing is given by the product of mass, length, gravitational acceleration, and the cosine of the leg angle from vertical:

$$T_{supp} = M \cdot L \cdot g \cdot \cos\theta$$

Figure 9A:
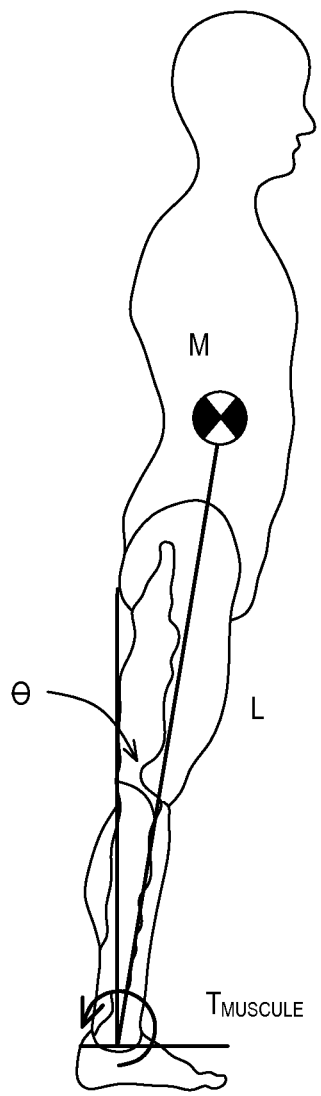
FIG. 9A shows a schematic of muscle volume scaling.

If length and subject height scale together, it follows that muscle volume scales linearly with body mass and height. Both the analytical model and the MRI-based volume results (FIG. 9B) support a mass-height scaling for lower limb muscle volume. This relationship was statistically more correlative than a scaling by mass or height alone. When the results for healthy active subjects were compared to literature values for cadaver muscle architecture [7], the cadavers' lower limb muscle volume was less than half of what would be expected from a healthy subject of the same mass and height (FIG. 9A). This result may explain why previous musculoskeletal models based on cadaver lower limb architecture have had to scale peak isometric tension by 200% in order to produce in vivo isometric joint moments [8].

Figure 10A:
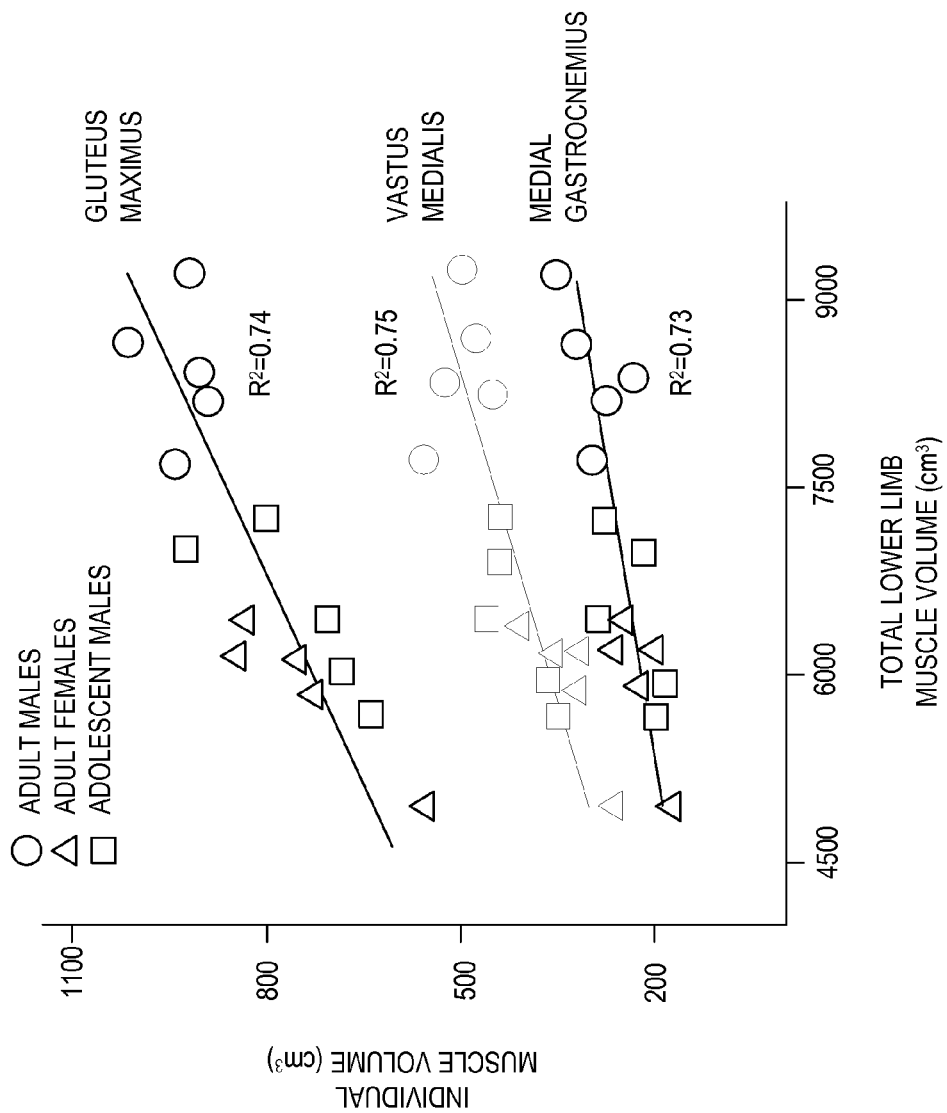
FIGS. 10A and 10B show scaling relationships for muscles in the lower limb, where
Figure 10B:
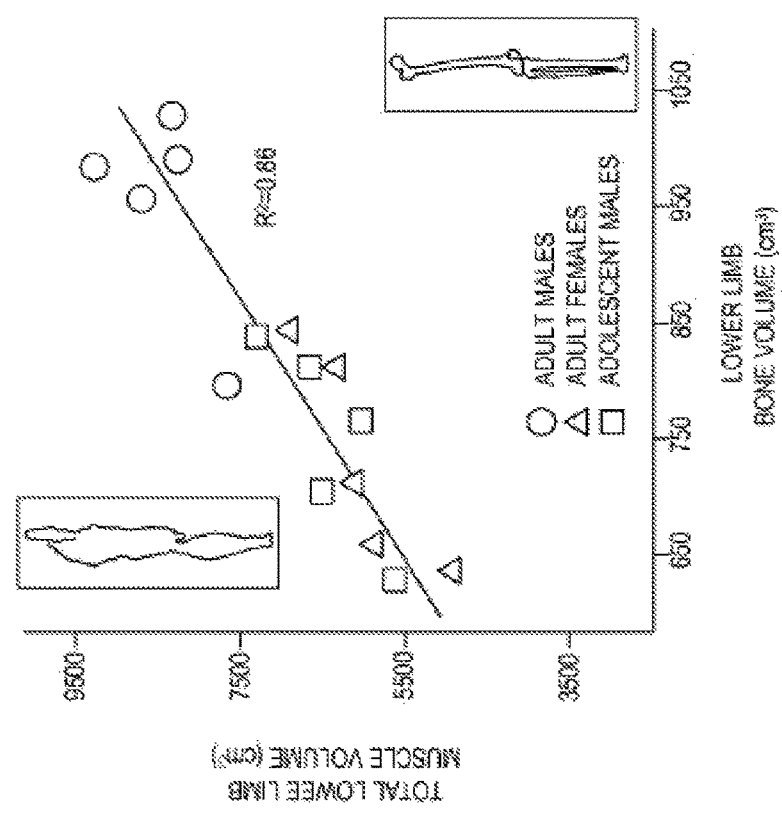

For individual muscles of the lower limb there is a statistical correlation between total lower limb muscle volume and the volume of the individual muscle. Three examples are given (FIG. 10A). The linear regressions shown here can be thought of as muscle fraction averages for our population. On average, each of the subjects' muscles represents a constant proportion of their total lower limb musculature. For the entire population included in the study for this Example, a statistical correlation between total muscle volume and total bone volume of the lower limb was observed (FIG. 10B). The muscles and bones of a limb are inextricably mechanically linked in movement and locomotion. A linear scaling exists between these parameters for a subject population that ranges in age, size, and sex. The work according to this Example demonstrates scaling relationships that exist for muscle volumes across healthy adult and adolescent populations. Lower limb muscle and bone volumes scale together, as do individual muscles contained in the limb. Furthermore, these results suggest that muscle volumes scale linearly with height and mass across individuals. This height-mass scaling relationship can be used to approximate healthy subject muscle volume from height and mass or compare patients' muscle volumes against those observed in a healthy population.

Figure 9B:
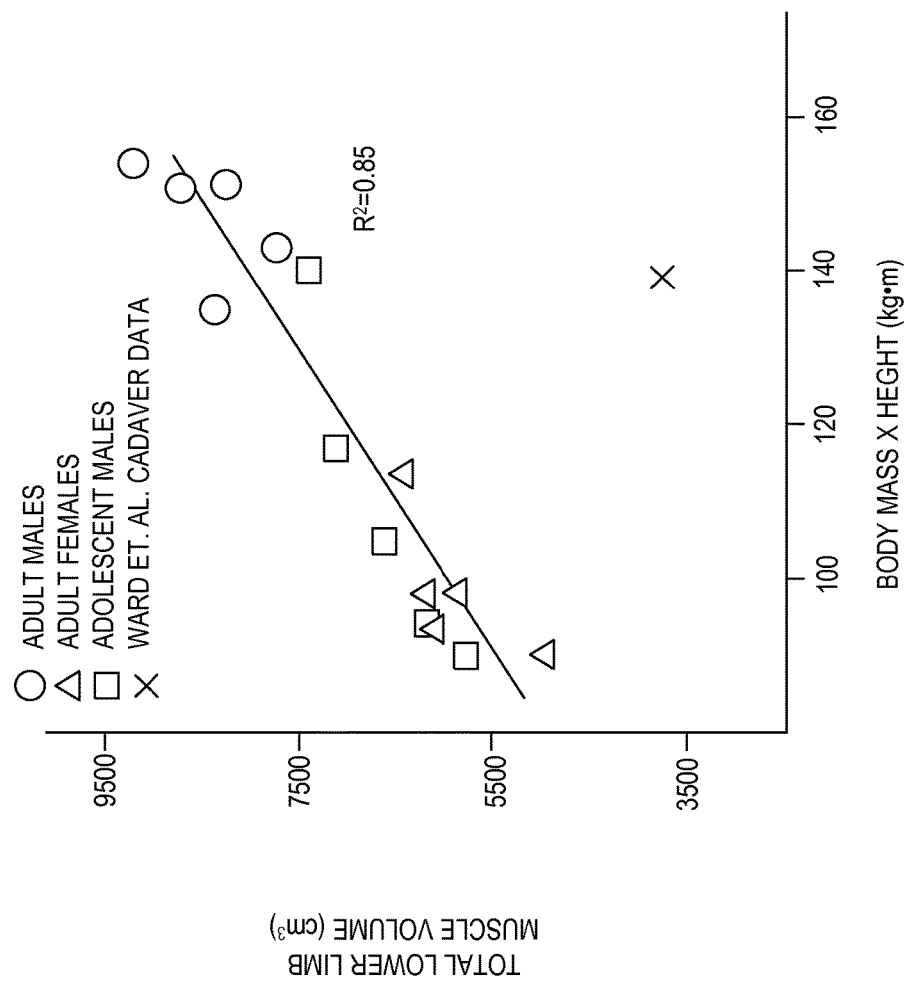
FIG. 9B shows a plot of lower limb muscle volume as a function of body mass×height, in accordance with one embodiment presented herein.

Referring specifically to FIGS. 9 and 10, FIG. 9A shows a schematic of the mechanical principle of muscle volume scaling. The quantity of lower limb muscle needed to support and move a subject will be a function of both the mass of the subject and the length over which the muscle(s) are acting on the center of mass. FIG. 9B shows a plot of lower limb muscle volume as a function of body mass×height. Literature value [3] for cadaver muscle volume vs. height and mass is shown (X). FIG. 10 shows scaling relationships for muscles in the lower limb. In particular, FIG. 10A shows linear scalings for muscles crossing the three joints in the lower limb; the volume of each muscle can be well-approximated as a constant proportion of the total lower limb musculature. FIG. 10B illustrates the linear relationship between muscle volume and bone volume for subjects ranging in age and body size.

The results of the implementations discussed above, among other advantages, may provide more information on how muscle sizes may scale across individuals, to show how muscle volumes scale with height and mass, how individual muscle volumes scale relative to each other, and how muscle volumes scale with bone volume.

Example 4

Figure 11:
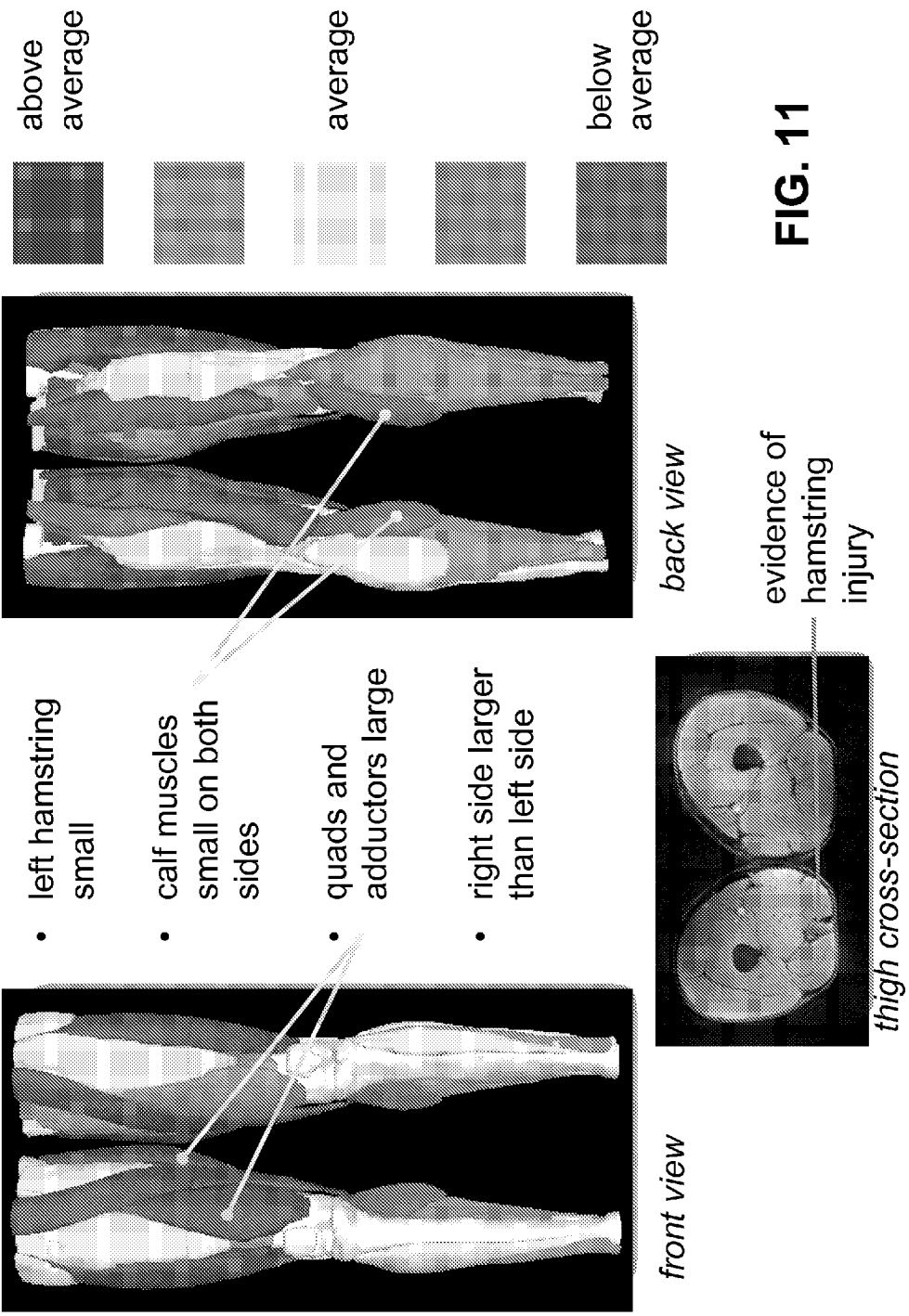
FIG. 11 shows muscles in lower limbs of an elite athlete, and slice images, illustrating muscle volumes of the athlete as compared to normal subjects, in accordance with one embodiment presented herein.
Figure 12A:
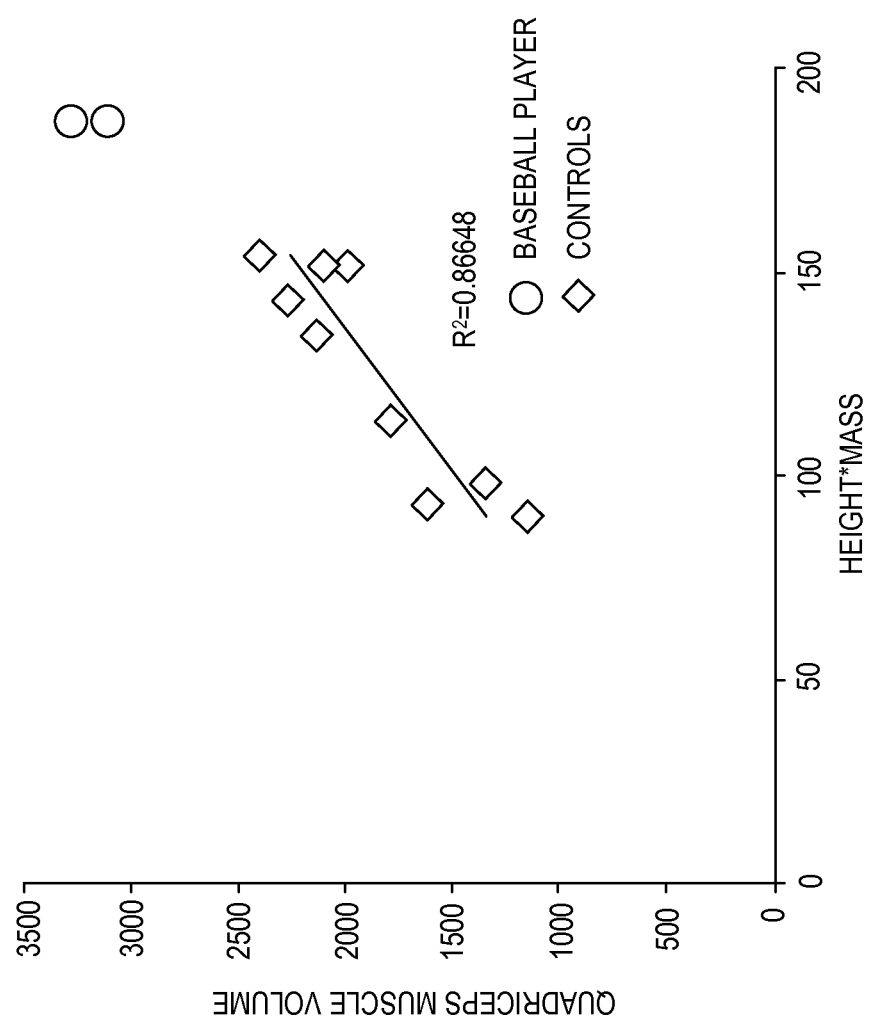
FIGS. 12A and 12B show plots of linear relationships between mass-height and muscle volume for various individuals of a sample population, in accordance with one embodiment presented herein.
Figure 12B:
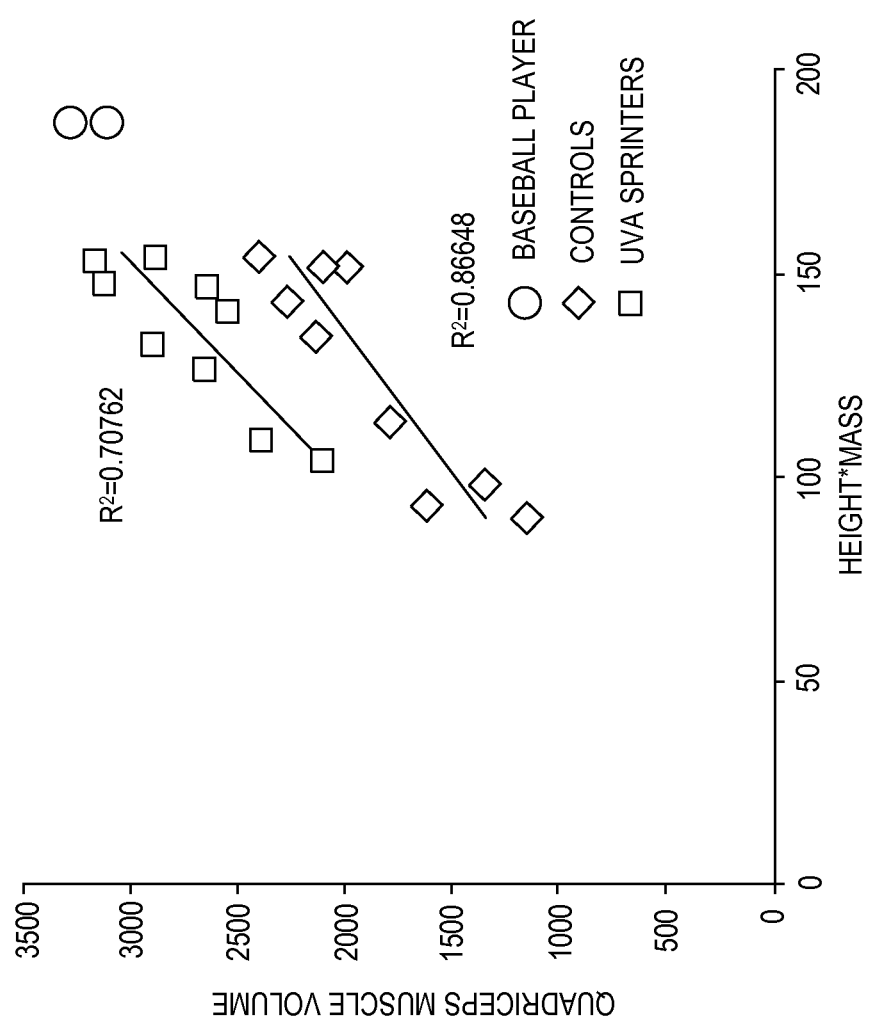

This Example shows data and illustrations resulting from imaging of lower limbs of an elite athlete. FIG. 11 shows labeled abnormalities in various muscle volumes and/or size. The models shown correspond to a professional baseball player with muscle function and overall physical and athletic performance that generally exceeds that of the normal population. However, illustrations also show that the athlete has a hamstring injury, and thereby certain specific muscle(s) exhibit abnormalities. As can be seen in FIG. 11, the image reconstructions of the front view and back view of the lower limb of the athlete show that the left hamstring is smaller than that associated with a normal population, the calf muscles are small on both sides, the quads and adductors are large, and the right side is larger than the left side. The color blocks shown on the right side indicate the relative volume/size of each of the illustrated muscles, where dark blue (top) represents above average in comparison to the normal population, light blue (second from top) represents between above average and average, yellow (middle) represents average, orange (second from bottom) represents between average and below average, and red (bottom) represents below average. FIG. 11 shows that, as discussed above, although some muscles modeled and illustrated have relative small or large volume/size that could correspond with enhanced function, the athlete of this Example also has a hamstring injury proximate certain muscles, as evidenced by the thigh cross-section slice image. FIGS. 12A and 12B show a linear regression analysis for data corresponding to the linear correlation of muscle volume of quadriceps in a sample population of controls (normal population of healthy individuals) in comparison to baseball players and also (in FIG. 12B) collegiate sprinters.

The information provided according to the plots and data modeling and imaging according to this Example can provide data for clinicians such as sports medicine professionals to effectively and accurately discern enhanced aspects of musculoskeletal structures of elite athletes such as professional and college athletes, as compared to normal individuals. Aspects practiced according to this Example provide advantageous and accurate tools for measuring, diagnosing, and studying the nature of enhanced muscle function, and accordingly may support and equip clinicians for adjusting or designing particular rehabilitation strategies or other procedures for studying and/or correcting muscle abnormalities in both individuals having enhanced muscle performance and/or the normal population, or in individuals with particular muscle impairments.

Based on the foregoing, it should be appreciated that concepts and technologies for identification of muscle abnormalities are provided herein. Although the subject matter presented herein has been described in language specific to structural features and methodological acts, it is to be understood that the invention defined in the appended claims is not necessarily limited to the specific features or acts described herein. Rather, the specific features and acts are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

LIST OF REFERENCES

[1] Holzbaur, K. R., S. L. Delp, G. E. Gold, and W. M. Murray, Moment-generating capacity of upper limb muscles in healthy adults. *J Biomech*, 2007. 40(11): p. 2442-9.

[2] Hurley, M. V., The role of muscle weakness in the pathogenesis of osteoarthritis. *Rheum Dis Clin North Am*, 1999. 25(2): p. 283-98, vi.

[3] Moseley, J. B., K. O'Malley, N. J. Petersen, T. J. Menke, B. A. Brody, D. H. Kuykendall, J. C. Hollingsworth, C. M. Ashton, and N. P. Wray, A controlled trial of arthroscopic surgery for osteoarthritis of the knee. *N Engl J Med*, 2002. 347(2): p. 81-8.

[4] Tan H, Meyer C H. Estimation of k-space trajectories in spiral MRI. *Magn Reson Med.* 2009 June; 61(6):1396-404.

[5] Chen W, Sica C T, Meyer C H. Fast conjugate phase image reconstruction based on a Chebyshev approximation to correct for B0 field inhomogeneity and concomitant gradients. Magn Reson Med. 2008 November; 60(5): 1104-11.

[6] K R S Holzbaur et. al. *J Biomech* 40, 742-749, 2007.

[7] S R Ward et. al. *Clin Ortop Relat Res.* 467: 1074-1082, 2009.

[8] E M Arnold et. al. *Annals of Biomed. Eng.* 38, 2: 269-279, 2010.

[9] Chen W, Meyer C H. Semiautomatic off-resonance correction in spiral imaging. Magn Reson Med. 2008 May; 59(5):1212-9

[10] Meyer C H, Pauly J M, Macovski A, Nishimura D G. Simultaneous spatial and spectral selective excitation. Magn Reson Med. 1990 August; 15(2):287-304.

What is claimed is:

1. A method for identifying a muscle abnormality, comprising:
   acquiring image data from a magnetic resonance imaging (MRI) system, wherein the image data is associated with a plurality of muscles in an area of interest of a living subject;
   generating, by a computer system, a three-dimensional model of each individual muscle of the plurality of muscles based on segmentation of muscle bellies or muscle groups in the image data;
   calculating, by the computer system, at least one of the volume and length of one of the plurality of muscles based on the three-dimensional model of the muscle; and
   determining, by the computer system, if the at least one of the volume and length for the muscle, as calculated, deviates from at least one of the volume and length associated with a healthy muscle, wherein the healthy muscle is represented by a composite based on individual healthy muscles from a plurality of healthy living subjects in a sample population, and wherein the muscle and the individual healthy muscles are scaled by the product of mass and height of the respective subjects.

2. The method of claim 1, further comprising, upon determining that the at least one of the volume and length for the muscle deviates from the at least one of the volume and length associated with a healthy muscle, identifying a muscle abnormality based on the deviation.

3. The method of claim 2, wherein identifying a muscle abnormality comprises determining if the deviation exceeds a threshold deviation associated with a muscle abnormality.

4. The method of claim 2, wherein identifying a muscle abnormality based on the deviation comprises calculating a deviation factor corresponding to at least one of the amount or degree of the deviation and determining if the calculated deviation factor corresponds to a deviation factor associated with a muscle abnormality.

5. The method of claim 2, further comprising generating a visual representation of the muscle and the deviation.

6. The method of claim 5, further comprising:
   generating, by the computer system, a report that identifies which muscles have normalized volumes and/or lengths that are different from the healthy muscle by at least one standard deviation.

7. The method of claim 6, wherein the report is a colormap that displays a number of standard deviations that the living subject's muscle volume deviates from the mean healthy muscle volume for the plurality of muscles.

8. The method of claim 1, wherein acquiring the image data comprises acquiring a spiral MRI scan of the area of interest of the living subject using the MRI system.

9. The method of claim 8, wherein acquiring the spiral MRI scan includes k-space trajectory estimation and off-resonance correction.

10. The method of claim 1, wherein the area of interest of the living subject comprises at least one of a limb and a joint.

11. The method of claim 1, wherein acquiring the image data comprises a gradient-echo MRI scan of the area of interest of the living subject using the MRI system.

12. The method of claim 1, wherein the muscle abnormality corresponds to enhanced muscle performance.

13. The method of claim 1, wherein the muscle abnormality corresponds to muscle impairment.

14. A non-transitory computer-readable storage medium having stored thereon computer-executable instructions which, when executed by one or more processors, cause a computer to:
   acquire image data from a magnetic resonance imaging (MRI) system, wherein the image data is associated with a plurality of muscles in an area of interest of a living subject;
   generate a three-dimensional model of each individual muscle of the plurality of muscles based on segmentation of muscle bellies or muscle groups in the image data;
   calculate at least one of the volume and length of one of the plurality of muscles based on the three-dimensional model of the muscle; and
   determine if the at least one of the volume and length for the muscle, as calculated, deviates from at least one of the volume and length associated with a healthy muscle, wherein the healthy muscle is represented by a composite based on individual healthy muscles from a plurality of healthy living subjects in a sample population, and wherein the muscle and the individual healthy muscles are scaled by the product of mass and height of the respective subjects.

15. The non-transitory computer-readable storage medium of claim 14, further comprising computer-executable instructions which, when executed by the one or more processors, cause the computer to, upon determining that the at least one of the volume and length for the muscle deviates from the at least one of the volume and length associated with a healthy muscle, identify a muscle abnormality based on the deviation.

16. The non-transitory computer-readable storage medium of claim 15, wherein identifying a muscle abnormality based on the deviation comprises determining if the deviation exceeds a threshold deviation associated with a muscle abnormality.

17. The non-transitory computer-readable storage medium of claim 15, wherein identifying a muscle abnormality based on the deviation comprises calculating a deviation factor corresponding to at least one of the amount or degree of the deviation and determining if the calculated deviation factor corresponds to a deviation factor associated with a muscle abnormality.

18. The non-transitory computer-readable storage medium of claim 15, further comprising computer-executable instructions which, when executed by the one or more processors, cause the computer to generate a visual representation of the muscle and the deviation.

19. The non-transitory computer-readable storage medium of claim 18, further comprising computer-executable instructions which, when executed by the one or more processors, cause the computer to, generate a report that identifies which muscles have normalized volumes and/or lengths that are different from the healthy muscle by at least one standard deviation.

20. The non-transitory computer-readable storage medium of claim 19, wherein the report is a colormap that displays a number of standard deviations that the living subject's muscle volume deviates from the mean healthy muscle volume for the plurality of muscles.

21. The non-transitory computer-readable storage medium of claim 18, wherein acquiring the image data comprises receiving image data associated with a gradient-echo MRI scan of the area of interest of the living subject.

22. The non-transitory computer-readable storage medium of claim 18, wherein the muscle abnormality corresponds to enhanced muscle performance.

23. The non-transitory computer-readable storage medium of claim 18, wherein the muscle abnormality corresponds to muscle impairment.

24. The non-transitory computer-readable storage medium claim 14, wherein acquiring the image data comprises receiving image data associated with at least one spiral MRI scan of the area of interest of the living subject.

25. The non-transitory computer-readable storage medium of claim 14, wherein the area of interest of the living subject comprises at least one of a limb and a joint.

26. A system for identifying a muscle abnormality comprising:
one or more processing units;
a memory device operatively coupled to the one or more processing units; and
a program module residing in the memory device and configured, when executed, to cause the one or more processing units to:
acquire image data associated with a plurality of muscles in an area of interest of a living subject;
generate a three-dimensional model of each individual muscle of the plurality of muscles based on segmentation of muscle bellies or muscle groups in the image data;
calculate at least one of the volume and length of one of the plurality of muscles based on the three-dimensional model of the muscle; and
determine if the at least one of the volume and length for the particular muscle, as calculated, deviates from at least one of the volume and length associated with a healthy muscle, wherein the healthy muscle is represented by a composite based on individual healthy muscles from a plurality of healthy living subjects in a sample population, and wherein the muscle and the individual healthy muscles are scaled by the product of mass and height of the respective subjects.

27. The system of 26, wherein the program module is further configured to cause the one or more processing units to,
upon determining that the at least one of the volume and length for the muscle deviates from the at least one of the volume and length associated with a healthy muscle,
calculate a deviation factor corresponding to at least one of the amount and degree of the deviation, and
identify a muscle abnormality based on the calculated deviation factor.

28. The system of claim 27, wherein the program module is further configured to cause the one or more processing units to generate a visual representation of the muscle and the deviation factor.

29. The system of claim 28, wherein the program module is further configured to cause the one or more processing units to generate a report that identifies which muscles have normalized volumes and/or lengths that are different from the healthy muscle by at least one standard deviation.

30. The system of claim 29, wherein the report is a colormap that displays a number of standard deviations that the living subject's muscle volume deviates from the mean healthy muscle volume for the plurality of muscles.

31. The system of claim 27, wherein identifying the muscle abnormality comprises determining if the calculated deviation factor corresponds to a deviation factor associated with a muscle abnormality.

32. The system of claim 26, wherein acquiring the image data comprises receiving image data associated with at least one spiral MRI scan of the area of interest of the living subject.

33. The system of claim 26, wherein the area of interest of the living subject comprises at least one of a limb and a joint.

34. The system of claim 26, wherein acquiring the image data comprises receiving image data associated with a gradient-echo MRI scan of the area of interest of the living subject.

35. The system of claim 26, wherein the muscle abnormality corresponds to enhanced muscle performance.

36. The system of claim 26, wherein the muscle abnormality corresponds to muscle impairment.

* * * * *